(12) United States Patent
McCracken et al.

(10) Patent No.: US 10,512,746 B2
(45) Date of Patent: Dec. 24, 2019

(54) SNAP-IN ELBOW FOR PATIENT INTERFACE MASK

(71) Applicant: KONINKLIJKE PHILIPS N.V., Eindhoven (NL)

(72) Inventors: Christopher James McCracken, Harrison City, PA (US); Robert Earl Hieber, Export, PA (US)

(73) Assignee: Koninklijke Philips N.V., Eindhoven (NL)

( * ) Notice: Subject to any disclaimer, the term of this patent is extended or adjusted under 35 U.S.C. 154(b) by 746 days.

(21) Appl. No.: 15/034,877

(22) PCT Filed: Oct. 29, 2014

(86) PCT No.: PCT/IB2014/065677
§ 371 (c)(1),
(2) Date: May 6, 2016

(87) PCT Pub. No.: WO2015/068081
PCT Pub. Date: May 14, 2015

(65) Prior Publication Data
US 2016/0279370 A1     Sep. 29, 2016

Related U.S. Application Data

(60) Provisional application No. 61/902,336, filed on Nov. 11, 2013.

(51) Int. Cl.
*A61M 16/08* (2006.01)
*A61M 16/06* (2006.01)
*A61M 16/20* (2006.01)

(52) U.S. Cl.
CPC ........ *A61M 16/0816* (2013.01); *A61M 16/06* (2013.01); *A61M 16/0616* (2014.02);
(Continued)

(58) Field of Classification Search
CPC ...... A61M 16/06–0694; A61M 16/0816–0858
See application file for complete search history.

(56) References Cited

U.S. PATENT DOCUMENTS 8,528,561 B2 * 9/2013 Ng ................ A61M 16/06
128/206.28
2007/0044804 A1 * 3/2007 Matula, Jr. ........... A61M 16/06
128/206.21
(Continued)

FOREIGN PATENT DOCUMENTS

GB          2480288 A       11/2011
WO     WO2009108995 A1      9/2009
(Continued)

*Primary Examiner* — Valerie L Woodward
(74) *Attorney, Agent, or Firm* — Michael W. Haas

(57) ABSTRACT

A ventilation mask (10) includes a mask body (100), a frame (200) and an elbow (300). The mask body has a first opening (130) and a sealing member (110) configured to engage the face of a patient so as to surround at least a mouth and a nose of the patient. The frame is connected to an outer surface of the mask body, and has an interface member (220) configured to interlock with the mask body at the first opening. The elbow has a first end (310) connectable with a gas supply, and a second end (320) configured to be fixedly secured to the interface member of the frame and to enable flow of gas from the elbow into the mask body through the first opening.

14 Claims, 7 Drawing Sheets

(52) U.S. Cl.
CPC ........ *A61M 16/0638* (2014.02); *A61M 16/20* (2013.01); *A61M 16/0683* (2013.01); *A61M 16/0858* (2014.02); *A61M 16/208* (2013.01); *A61M 2207/00* (2013.01)

(56) References Cited

U.S. PATENT DOCUMENTS

| | | | |
|---|---|---|---|
| 2008/0066755 A1 | 3/2008 | Janbakhsh | |
| 2009/0223523 A1 | 9/2009 | Chang | |
| 2009/0241961 A1* | 10/2009 | McAuley | A61M 16/06 128/205.25 |
| 2012/0138061 A1* | 6/2012 | Dravitzki | A61M 16/06 128/205.25 |
| 2012/0234326 A1 | 9/2012 | Mazzone | |
| 2013/0213402 A1 | 8/2013 | D'souza | |
| 2014/0174446 A1* | 6/2014 | Prentice | A61M 16/06 128/205.25 |

FOREIGN PATENT DOCUMENTS

| | | | |
|---|---|---|---|
| WO | WO2011060479 A1 | 5/2011 | |
| WO | WO-2011110968 A2 * | 9/2011 | ............ A61M 16/06 |
| WO | WO2013006065 A1 | 1/2013 | |
| WO | WO2013066195 A1 | 5/2013 | |
| WO | WO2013068911 A1 | 5/2013 | |

\* cited by examiner

SNAP-IN ELBOW FOR PATIENT INTERFACE MASK

CROSS-REFERENCE TO RELATED APPLICATIONS

This patent application claims the priority benefit under 35 U.S.C. § 371 of international patent application no. PCT/IB2014/065677, filed Oct. 29, 2014, which claims the priority benefit under 35 U.S.C. § 119(e) of U.S. Provisional Application No. 61/902,336 filed on Nov. 11, 2013, the contents of which are herein incorporated by reference.

TECHNICAL FIELD

The present invention is directed generally to a continuous positive airway pressure (CPAP) or non-invasive ventilation (NIV) patient interface mask. More particularly, various inventive apparatuses and assembly methods disclosed herein relate to ventilation masks and assembly methods of ventilation masks in which a circuit connection elbow is attached from an inside of a mask body to an interface member of a frame connected to an outer surface of the mask body.

BACKGROUND

Existing ventilation mask designs use a connection elbow or other rotating connections such as swivel adapters for attachment of a breathing circuit to the exterior of a ventilation mask. Attachment of connection elbows to a ventilation mask may be achieved by either snap connections or separate components such as snap rings. For example, existing ventilation masks may include connection elbows having tapered connections with a hub in the main body of the ventilation mask, where the connection elbow is inserted into the hub from outside the ventilation mask. Other existing ventilation masks may include connection elbows assembled from the outside of the ventilation mask by a C-clip attached inside the ventilation mask. Still further existing ventilation masks may include connection elbows assembled to the outside of the ventilation mask using snaps with or without push button releases.

However, if a large torque is applied to the connection elbows of the existing ventilation masks as described, the connection elbow may become disconnected from the ventilation mask and the connection between the breathing circuit and the ventilation mask may consequently fail, resulting in total loss of therapy. Also, as the air pressure inside the ventilation mask increases, the connection elbow can be pushed out from the ventilation mask, causing a small leak.

It would be desirable to provide a ventilation mask and an assembly method of a ventilation mask that would prevent disconnection between a breathing circuit and the ventilation mask, and that would prevent occurrence of small leaks from the ventilation mask at the elbow connection.

SUMMARY

The present disclosure is directed to ventilation masks and methods of assembling ventilation masks.

Generally, in one aspect, a ventilation mask includes a mask body having a first opening, and a sealing member configured to engage a face of a patient so as to surround at least a mouth and/or a nose of the patient; a frame connected to an outer surface of the mask body and having an interface member configured to interlock with the mask body at the first opening; and an elbow having a first end connectable with a gas supply, and a second end configured to be fixedly secured to the interface member of the frame and to enable flow of gas from the elbow into the mask body through the first opening.

In one or more embodiments, the frame may include a base member configured to interlock with and conformally fit around sidewalls of the mask body.

In one or more embodiments, a plurality of under-cuts may be disposed along the sidewalls of the mask body, and the plurality of under-cuts may be configured to interlock with the base member of the frame.

In one or more embodiments, the frame may include a plurality of rib members that extend between the interface member and the base member.

In one or more versions of these embodiments, the sidewalls of the mask body may further include a plurality of recessed areas, and the plurality of rib members may be configured to have conforming shape so as to tightly press-fit within the plurality of recessed areas.

In one or more versions of these embodiments, the interface member may be ring-shaped, and the elbow may include an outer wall having at least one snap protrusion near the second end, the at least one snap protrusion configured to interlock with the interface member.

In one or more versions of these embodiments, the mask body may include a grooved portion disposed around the first opening, and the interface member may include a protruding flange configured so as to be press-fit within the grooved portion to interlock and seal the interface member with the mask body.

In one or more embodiments, the second end of the elbow may have a flange configured to hold the grooved portion of the mask body against the protruding flange of the interface member.

In one or more embodiments, the at least one snap protrusion may include a plurality of snap protrusions equally spaced apart from each other along a periphery of the outer wall of the elbow.

In one or more embodiments, the ventilation mask may further include a pad member configured to engage a forehead of the patient so as to stabilize a position of the ventilation mask on the patient; and an arm member connecting the pad member to the frame.

In one or more embodiments, the ventilation mask may further include a hinge connecting the pad member to the arm member so that the mask body and the frame can be moved away from the face of the patient to expose at least the mouth and the nose while the pad member remains secured to the forehead.

In one or more embodiments, the elbow may be an entrainment elbow.

In one or more embodiments, the elbow may be an entrainment-exhalation elbow.

In one or more embodiments, the mask body and the frame may be made of silicone.

In another aspect, a ventilation mask may include a mask body having a first opening and configured to engage a face of a patient so as to surround at least a mouth and/or a nose of the patient; a frame connected to an outer surface of the mask body and configured to rigidly support the mask body, the frame including an interface member configured to interlock with the mask body at the first opening, a base member configured to interlock with and conformally around sidewalls of the mask body, and a plurality of rib members that extend between the interface member and the base member; and an elbow having a first end connectable with a gas supply, and a second end configured to be fixedly secured to the interface member of the frame and to enable flow of gas from the elbow into the mask body through the first opening.

In one or more embodiments, the sidewalls of the mask body may include a plurality of recessed areas, and the plurality of rib members are configured to have conforming shape so as to tightly press-fit within the plurality of recessed areas.

In one or more embodiments, the elbow may include an outer wall having a plurality of snap protrusions equally spaced from each other along a periphery of the outer wall, the plurality of snap protrusions configured to interlock with the interface member.

In one or more embodiments, the mask body may include a grooved portion disposed around the first opening, and the interface member may include a protruding flange configured so as to be press-fit within the grooved portion to interlock and seal the interface member with the mask body.

In one or more versions of these embodiments, the ventilation mask may further include a pad member configured to engage a forehead of the patient so as to stabilize a position of the ventilation mask on the patient; an arm member having a first end and a second end opposite the first end, the first end connected to the base member of the frame; and a hinge connecting the pad member to the second end of the arm member so that the mask body and the frame can be moved away from the face of the patient to expose at least the mouth and the nose while the pad member remains secured to the forehead.

In another aspect, a method of assembling a ventilation mask including a mask body having a first opening, a frame having an interface member, and an elbow, the method including connecting the frame to an outer surface of the mask body and so that the interface member is interlocked with the mask body at the first opening; pulling a first end of the elbow from inside the mask body through the first opening and the interface member; and fixedly securing a second end of the elbow to the interface member.

In one or more embodiments, the mask body may include a grooved portion disposed around the first opening, and the interface member may include a protruding flange, the connecting including press-fitting the protruding flange within the grooved portion to interlock and seal the interface member with the mask body.

In one or more embodiments, the second end of the elbow may have a flange, wherein the fixedly securing includes holding the grooved portion against the protruding flange of the interface member with the flange.

In one or more embodiments, the frame may include a base member, and a plurality of undercuts are disposed along sidewalls of the mask body, the connecting including interlocking the base member with the plurality of undercuts.

In one or more embodiments, the elbow may include a plurality of snap protrusions equally spaced apart from each other along a periphery of the outer wall near the second end, the fixedly securing including interlocking the plurality of snap protrusions with the interface member.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

In the following detailed description, for purposes of explanation and not limitation, representative embodiments disclosing specific details are set forth in order to provide a thorough understanding of the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatuses and methods may be omitted so as to not obscure the description of the representative embodiments. Such methods and apparatuses are clearly within the scope of the present teachings.

In view of the foregoing, various embodiments and implementations of the present invention are directed to a ventilation mask and a method of assembling a ventilation mask.

Figure 1:
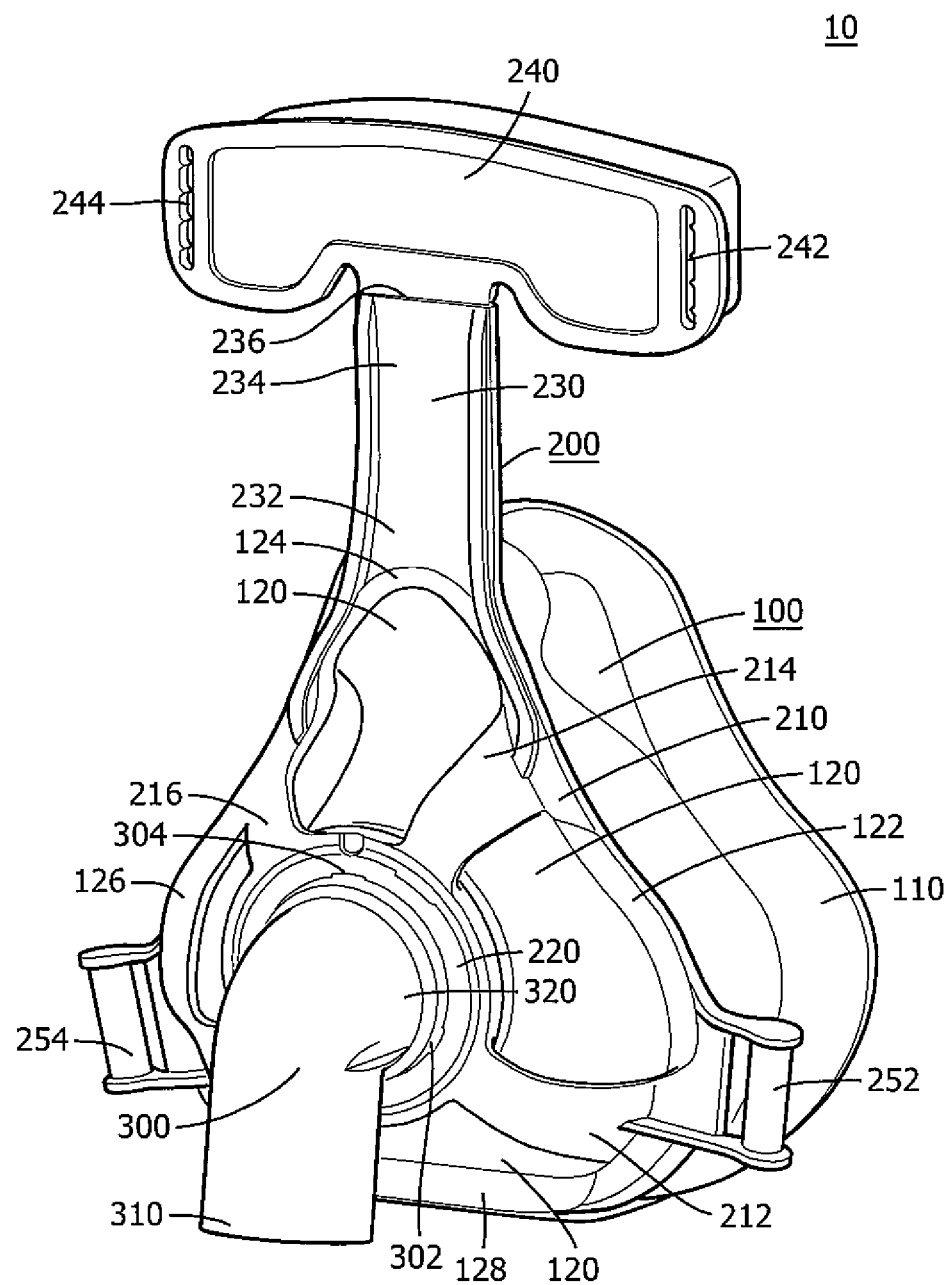
FIG. 1 illustrates a front perspective view of an assembled ventilation mask including a mask body, a frame and an elbow of an example embodiment.
Figure 2:
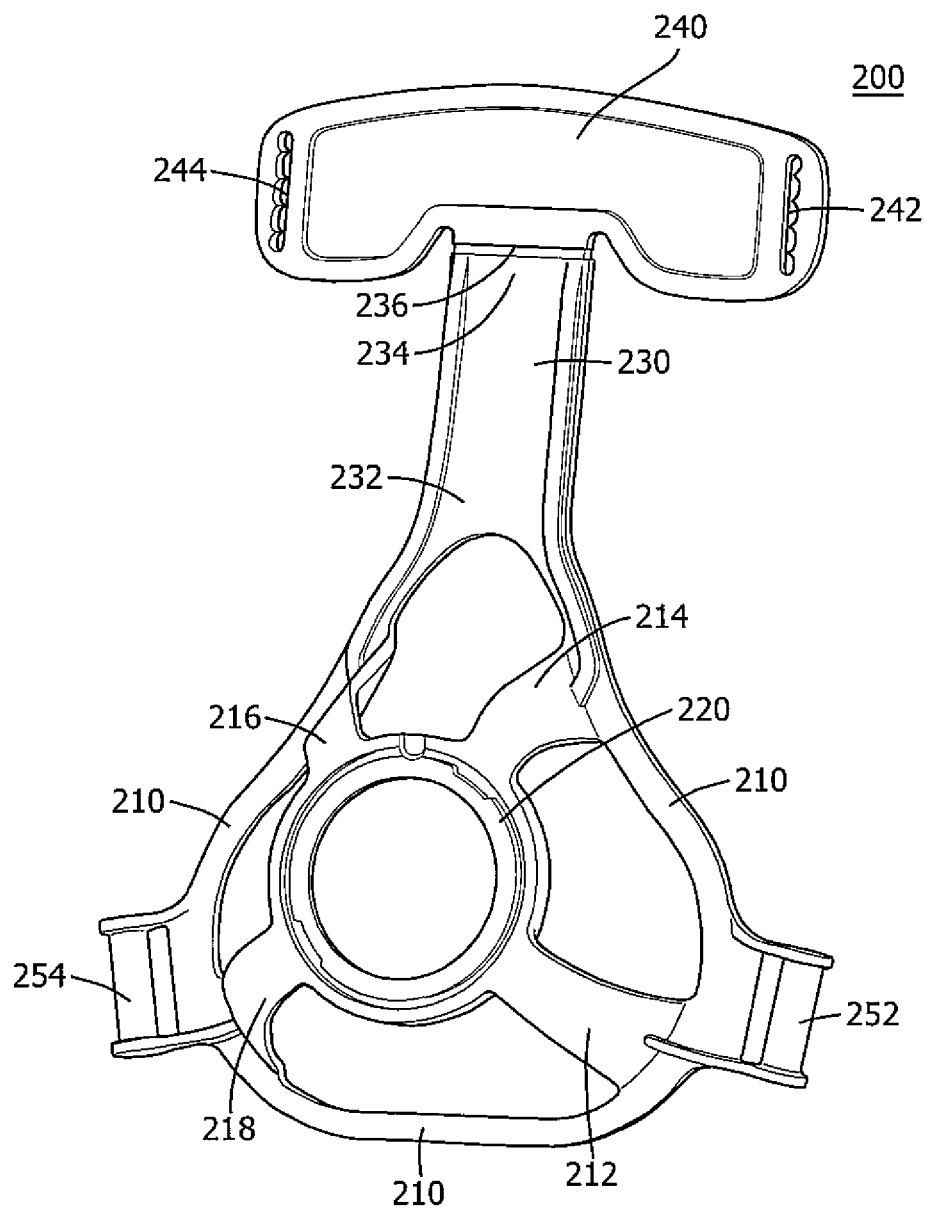
FIG. 2 illustrates a front perspective view of a frame of an example embodiment, prior to assembly of the ventilation mask.
Figure 3:
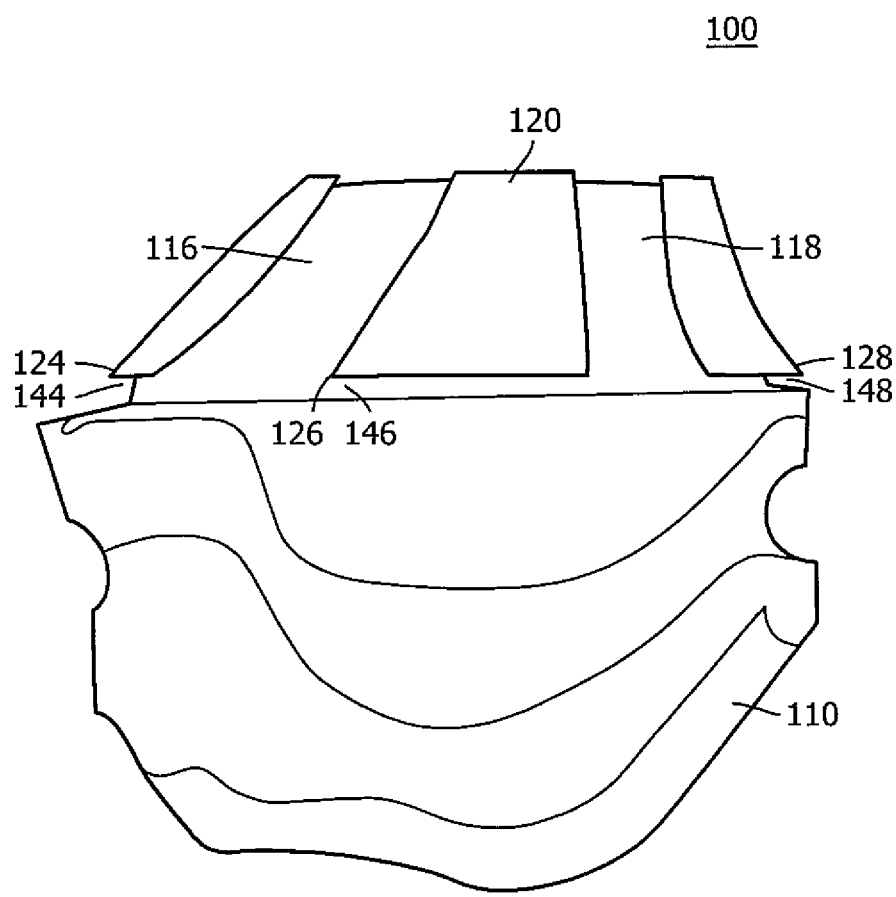
FIG. 3 illustrates a left side perspective view of a mask body of an example embodiment, prior to assembly of the ventilation mask.

FIG. 1 illustrates a front perspective view of assembled ventilation mask 10 including mask body 100, frame 200 and elbow 300 of an example embodiment. FIG. 2 illustrates a front perspective view of frame 200 prior to assembly of ventilation mask 10. FIG. 3 illustrates a left side perspective view of mask body 100 prior to assembly of ventilation mask 10.

As shown in FIGS. 1 and 3, mask body 100 may generally include sealing member 110 for sealingly engaging the face of a patient to surround at least a mouth and/or a nose of the patient, sidewalls 120, and over-hang sections 124, 126 and 128 that protrude outward from sidewalls 120 to form corresponding under-cuts or groove sections 144, 146 and 148 shown in FIG. 3. An additional under-cut (not shown) is also formed in relation to over-hang section 122 that protrudes outward from one of sidewalls 120 near the right-hand side of mask body 100 shown in FIG. 1. Mask body 100 may also include a first opening 130 (shown in FIG. 4) for reception of gas. Mask body 100 may be a somewhat pliant, flexible material such as silicone or the like, and may be clear, colorless or slightly opaque in whole or variously in part.

As shown in FIGS. 1 and 2, frame 200 may generally include interface member 220 which may be ring-shaped, base member 210, and a plurality of rib members 212, 214, 216 and 218. Rib members 212, 214, 216 and 218 extend between interface member 220 and base member 210. Rib members 212, 214, 216 and 218 may extend radially outward from interface member 220 to base member 210. Frame 200 further includes lower headgear connection point 252 which extends from base member 210 and rib member 212, and lower headgear connection point 254 which extends from base member 210 and rib member 218. The pair of lower headgear connection points 252 and 254 may connect with a strap or straps (not shown) fitted with VELCRO® or other hook-and-loop type attachments that pass therethrough, to secure assembled ventilation mask 10 to the head or neck of the patient. In other example embodiments, interface member 220 may be directly connected to base member 210 instead of by rib members 212, 214, 216 and 218, so that spaces or windows between the rib members may be excluded.

Frame 200 may further include pad member 240 which generally extends horizontally and includes upper headgear connection points 242 and 244 at opposite ends which also may connect with a strap or straps (not shown) fitted with VELCRO° or other hook-and-loop type attachments that pass therethrough. Pad member 240 may include foam padding on the underside that engages the forehead of the patient. Pad member 240 may stabilize a position of assembled ventilation mask 10 on the patient when tightly strapped in place. Arm member 230 of frame 200 has first end 232 and an opposite second end 234. First end 232 is connected to base member 210, and second end 234 is connected to pad member 240 via hinge 236. By loosening the strap or straps (not shown) connected to lower headgear connection points 252 and 254, arm member 230 may be pivoted with respect to pad member 240 about hinge 236, so that mask body 100 and the corresponding parts of frame 200 of assembled ventilation mask 10 can be moved away from the face of the patient to expose at least the mouth and nose of the patient while pad member 240 remains secured to the forehead of the patient. The patient may thus be provided with oral medication, food or drink without entirely removing ventilation mask 10 from the patient.

Frame 200 in general may be a somewhat rigid, inflexible material such as silicone or a plastic such as polypropylene. As further shown in FIG. 1, frame 200 of assembled ventilation mask 10 is connected to an outer surface of mask body 100 and rigidly supports mask body 100. Base member 210 is configured as having a shape that conforms with the shape of sidewalls 120 at an upper portion of mask body 100 and a thickness so as to fit tightly within under-cuts 144, 146 and 148 and the additional under-cut (not shown) of assembled ventilation mask 10.

Figure 5A:
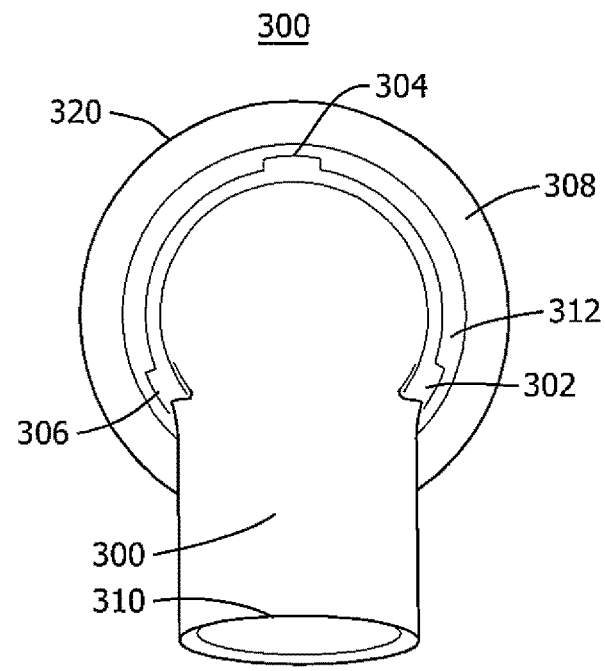
FIGS. 5A and 5B illustrate respective front and right side perspective views of an elbow of an example embodiment including a flange.

As also shown in FIG. 1, elbow 300 has first end 310 which may be frictionally connected to flexible tubing or conduit (not shown) to receive breathable gas from a ventilator, blower or CPAP machine (not shown). Elbow 300 also has second end 320. The cylindrical outer wall at second end 320 of elbow 300 may include a plurality of snap protrusions 302, 304 and 306 equally spaced apart from each other along the periphery of the cylindrical outer wall as shown in FIGS. 1 and 5A. Snap protrusions 302, 304 and 306 are configured to interlock with interface member 220 of assembled ventilation mask 10 to enable flow of breathable gas provided from the ventilator into mask body 100 through the flexible tubing, elbow 300 and first opening 130. Elbow 300 may be made of a rigid plastic material such as polypropylene or polycarbonate.

As shown in FIG. 3, sidewalls 120 of mask body also may include a plurality of recessed areas such as recessed areas 116 and 118. Recessed areas 116 and 118 may be configured to have conforming shape and depth so that respective rib members 216 and 218 may be tightly press-fit within recessed areas 116 and 118 to provide further connection between mask body 100 and frame 200 of assembled ventilation mask 10. Although not shown, recessed areas such as recessed areas 116 and 118 may also be formed in sidewalls 120 to receive rib members 212 and 214.

Figure 4:
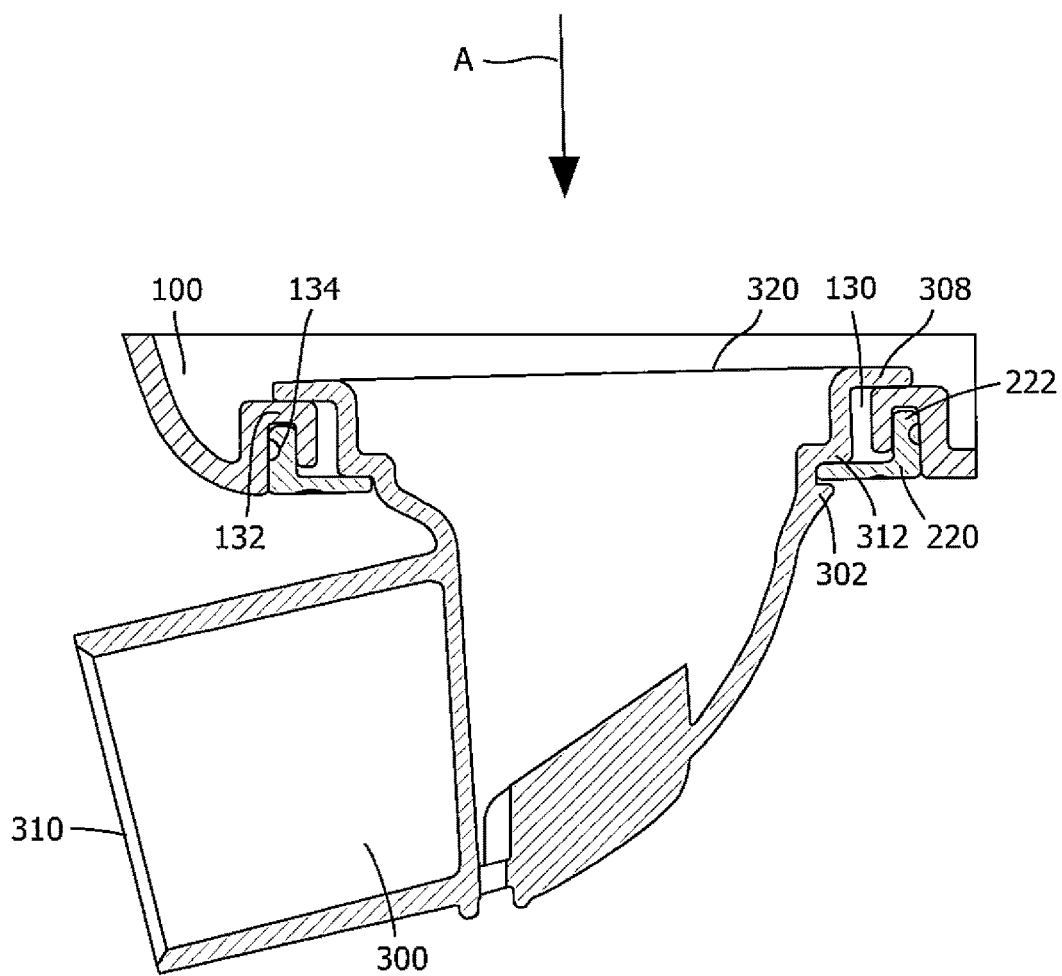
FIG. 4 illustrates a partial cross-sectional view of an assembled ventilation mask of an example embodiment, including the interface member of the frame interlocked with the mask body, and the elbow fixedly secured to the interface member of the frame.

FIG. 4 illustrates a partial cross-sectional view of assembled ventilation mask 10 including interface member 220 of frame 200 interlocked with mask body 100, and elbow 300 fixedly secured to interface member 220 of frame 200. As shown, mask body 100 includes first opening 130 which may be substantially circularly-shaped, and grooved portion 132 which may be disposed entirely around first opening 130. Interface member 220 of frame 200 may include a protruding flange 222 extending upwardly from its outer edge as shown in FIG. 4, so that flange 222 may be characterized as substantially having an L-shaped cross-section. Protruding flange 222 is configured to have shape and dimension so as to be press-fit within grooved portion 132 of mask body 100, to interlock and seal interface member 220 with mask body 100 of assembled ventilation mask 10. Bead 134 which may also be a somewhat pliant material such as silicone, may be formed on the inner wall of grooved portion 132 entirely around first opening 130. As protruding flange 222 is press-fit into grooved portion 132 bead 134 becomes compressed, providing an O-ring type seal between interface member 220 and mask body 100 of assembled ventilation mask 10.

As further shown in FIG. 4, snap protrusion 302 at second end 320 of elbow 300 is interlocked with interface member 220 of assembled ventilation mask 10. That is, interface member 220 is interlocked and secured between snap protrusion 302 and base 312 near second end 320. Although not shown in FIG. 4, snap protrusions 304 and 306 of elbow 300 are also interlocked with interface member 220. Additionally, elbow 300 may include a flange 308 extending upward and radially outward from the outer wall at base 112 near second end 320. Flange 308 may be configured to hold and force grooved portion 132 of mask body 100 against protruding flange 222 of interface member 220 once snap protrusions 302, 304 and 306 are interlocked in place with interface member 220 of assembled ventilation mask 10, to further secure and seal protruding flange 222 and grooved portion 132 together.

Figure 5B:
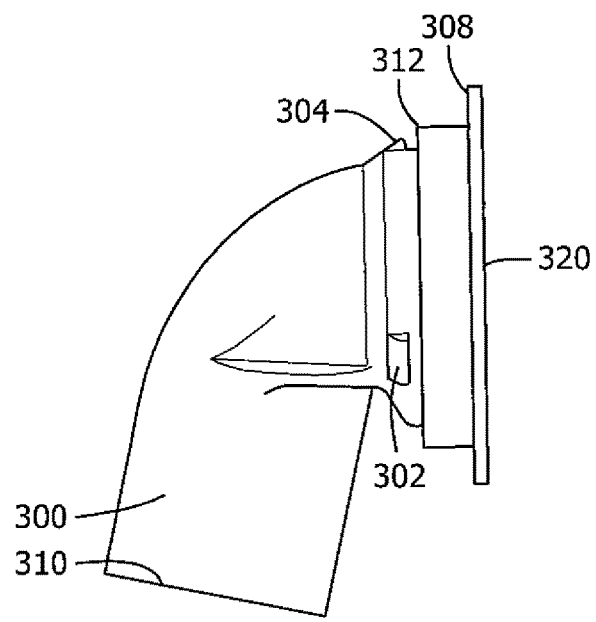

FIGS. 5A and 5B illustrate respective front and right side perspective views of elbow 300 including first and second ends 310 and 320, flange 308, base 312 and snap protrusions 302, 304 and 306 equally spaced apart from each other along the periphery of the cylindrical outer wall near second end 320. Although three snap protrusions 302, 304 and 306 are shown, in other embodiments elbow 300 may include any number of snap protrusions of various circumferential length spaced apart from each other along the periphery of the cylindrical outer wall. In other embodiments, a single continuous snap protrusion may be disposed around the entire periphery of the cylindrical outer wall.

Figure 6A:
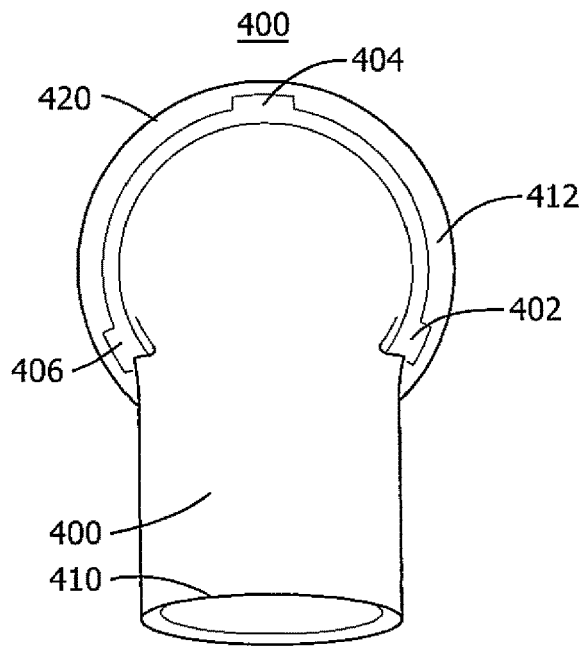
FIGS. 6A and 6B illustrate respective front and right side perspective views of an elbow of an example embodiment without a flange.
Figure 6B:
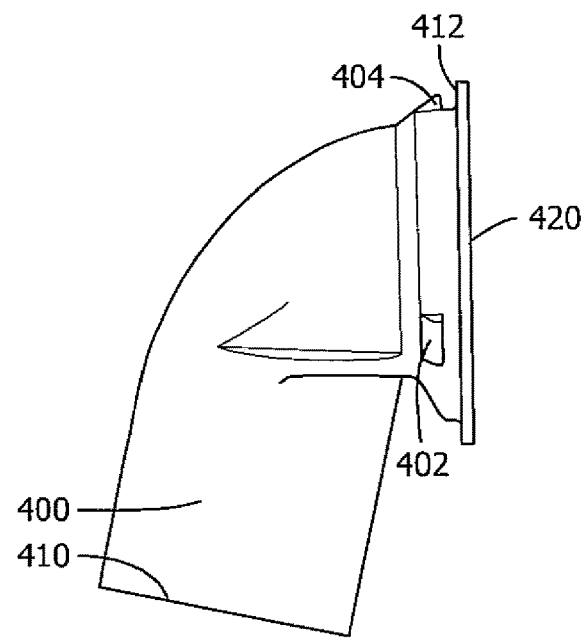

FIGS. 6A and 6B illustrate respective front and right side perspective views of elbow 400 without an elbow flange, according to a further example embodiment. Elbow 400 as shown includes first and second ends 410 and 420, base 412, and snap protrusions 402, 404 and 406 equally spaced apart from each other along the periphery of the cylindrical outer wall near second end 420. Although three snap protrusions 402, 404 and 406 are shown, in other embodiments elbow 400 may include any number of snap protrusions of various circumferential length spaced apart from each other along the periphery of the cylindrical outer wall. In other embodiments, a single continuous snap protrusion may be disposed around the entire periphery of the cylindrical outer wall. In other embodiments where elbow 400 is used in assembled ventilation mask 10 instead of elbow 300 such as shown in FIG. 4, protruding flange 222 is press-fit within grooved portion 132 to interlock and seal interface member 220 with mask body 100 of assembled ventilation mask 10 without being additionally held together by an elbow flange.

Figure 7:
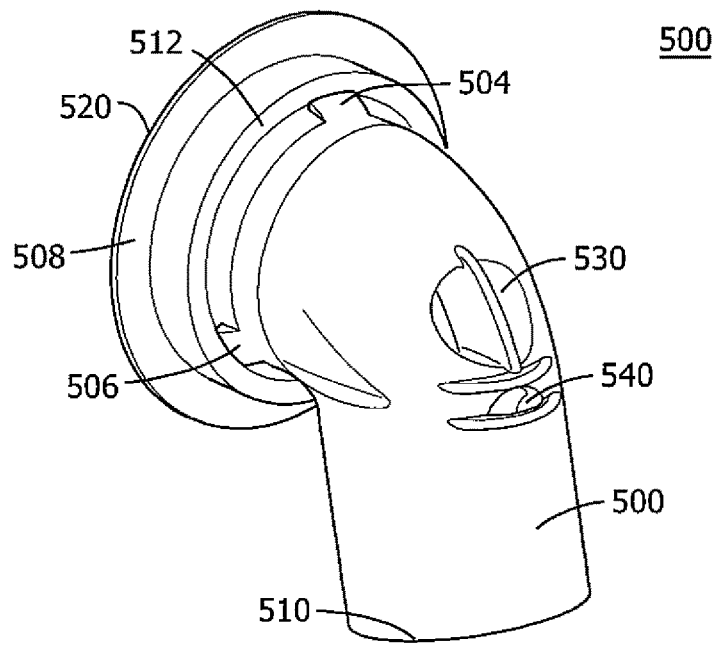
FIG. 7 illustrates a left side perspective view of an entrainment elbow of an example embodiment.

FIG. 7 illustrates a left side perspective view of entrainment elbow 500 of an example embodiment. Entrainment elbow 500 as shown includes first and second ends 510 and 520, snap protrusions 504 and 506 and at least one additional snap protrusion (not shown) such as snap protrusion 302 shown in FIGS. 5A and 5B, flange 508, base 512, entrainment valve opening 530 and entrainment valve flapper 540. As a safety feature, in the event that the ventilator, blower or CPAP machine (not shown) fail or power is disrupted, entrainment valve flapper 540 will release and open entrainment valve opening 530 to the atmosphere, enabling the patient to breathe. Entrainment elbow 500 may be used in assembled ventilation mask 10 in place of elbow 300 shown in FIGS. 1 and 4 for example, and in further example embodiments may be provided with any number of snap protrusions with or without flange 508.

Figure 8:
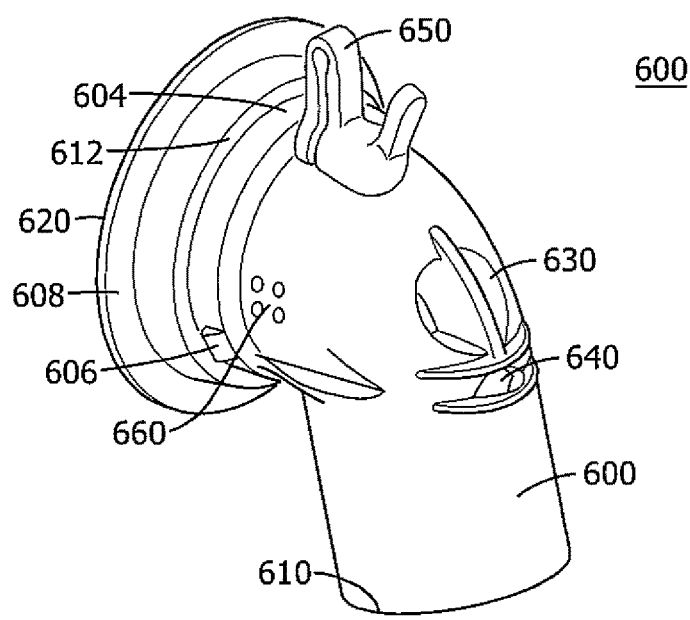
FIG. 8 illustrates a left side perspective view of an entrainment-exhalation elbow of an example embodiment.

FIG. 8 illustrates a left side perspective view of entrainment-exhalation elbow 600 of an example embodiment. Entrainment-exhalation elbow 600 as shown includes first and second ends 610 and 620, snap protrusions 604 and 606 and at least one additional snap protrusion (not shown) such as snap protrusion 302 shown in FIGS. 5A and 5B, flange 608, base 612, entrainment valve opening 630, entrainment valve flapper 640, cap 650 and exhalation holes 660. As described with respect to FIG. 7, as a safety feature entrainment valve flapper 640 will release and open entrainment valve opening 630 to the atmosphere, enabling the patient to breathe in the event of failure of the ventilator, blower or CPAP machine (not shown) or disruption of power. Additionally, cap 650 is a cap for a proximal pressure pick-off port which allows the connection of a flexible tube (not shown) for the purpose of measuring pressure inside assembled ventilation mask 10. The other end of the flexible tube may be connected to a ventilator or pressure monitoring device (not shown). Also, exhalation holes 660 flush exhaled carbon dioxide from entrainment-exhalation elbow 600. Entrainment-exhalation elbow 600 may be used in assembled ventilation mask 10 in place of elbow 300 shown in FIGS. 1 and 4 for example, and in further example embodiments may be provided with any number of snap protrusions with or without flange 608.

A method of assembling ventilation mask 10 will now be described with reference to FIGS. 1-4. Ventilation mask 10 may be considered as assembled from separate components including mask body 100, frame 200 and elbow 300. As described previously, mask body 100 may be made of a somewhat pliant, flexible material that may readily bend and be manipulated, while in contrast frame 200 may be made of a somewhat rigid, inflexible material.

Initially, elbow 300 as disconnected from flexible tubing or conduit of a breathing circuit may be inserted through first opening 130 and placed within the interior of mask body 100. Frame 200 may then be connected to the outer surface of mask body 100 by inserting corresponding portions of base member 210 into under-cuts or groove sections 144, 146 and 148 and any additional under-cuts. Protruding flange 222 may be press-fit within grooved portion 132 disposed around first opening 130 of mask body 100, so that interface member 220 may be interlocked and sealed with mask body 100 as bead 134 is compressed. Rib members 212, 214, 216 and 218 may be tightly press-fit into corresponding recessed areas such as recessed areas 116 and 118 shown in FIG. 3. Thereafter, first end 310 of elbow 300 previously placed within the interior of mask body 100 in a disconnected state may be grasped through the opening formed by interface member 220 and elbow 300 may be pulled from inside mask body 100 outward in the direction of arrow A shown in FIG. 4. Interface member 220 may slide along the outer wall of elbow 300 as elbow 300 is pulled from mask body 100, and may then slide over snap protrusions 302, 304 and 306, and into the space between snap protrusions 302, 304 and 306 and base 312. In this position, interface member may be interlocked with snap protrusions 302, 304 and 306. Also, flange 308 at second end 320 of elbow 300 holds grooved portion 132 of mask body 100 against protruding flange 222, further sealing interface member 220 and mask body 100.

In accordance with this example embodiment, since ventilation mask 10 may be assembled by pulling or manipulating elbow 300 from inside mask body 100 to interlock with interface member 220 from the inside out, therapy pressure created within mask body 100 during operation of ventilation mask 10 securely seals elbow 300 and mask body 100. Moreover, because elbow 300 is interlocked with interface member 220, which is a somewhat rigid, inflexible material, instead of directly to a more pliant material such as the material of mask body 100, elbow 300 may be more fixedly secured to ventilation mask 10, thus preventing disconnection of elbow 300 and preventing small leaks from ventilation mask 10 that may be caused by elbow 300 being pushed outward by therapy pressure during operation of ventilation mask 10.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

For example, assembled ventilation mask 10 may be configured to have a size and shape to surround both the mouth and the nose of the patient. In other example embodiments, ventilation mask 10 may be configured to have a size and shape to surround only the mouth of the patient, or only the nose of the patient.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 211.

The invention claimed is:

1. A ventilation mask comprising:
    a mask body having a first opening disposed about a central axis, and a sealing member configured to engage a face of a patient so as to surround at least a mouth and/or a nose of the patient;
    a frame connected to an outer surface of the mask body and having an interface member configured to interlock with the mask body at the first opening; and
    an elbow having a first end connectable with a gas supply, and a second end configured to be fixedly secured to the interface member of the frame and to enable flow of gas from the elbow into the mask body through the first opening,
    wherein the mask body comprises a grooved portion extending generally parallel to the central axis and disposed around the first opening,
    wherein the interface member comprises a protruding flange extending generally parallel to the central axis toward the grooved portion, the protruding flange being configured to be press-fit within the grooved portion to interlock and seal the interface member with the mask body, and wherein the second end of the elbow has a flange extending generally perpendicularly outward away from the central axis which is configured to hold the grooved portion of the mask body against the protruding flange of the interface member.

2. The ventilation mask of claim 1, wherein the frame comprises a base member configured to interlock with and conformally fit around sidewalls of the mask body.

3. The ventilation mask of claim 2, wherein a plurality of under-cuts are disposed along the sidewalls of the mask body, the plurality of under-cuts configured to interlock with the base member of the frame.

4. The ventilation mask of claim 3, wherein the frame comprises a plurality of rib members that extend between the interface member and the base member.

5. The ventilation mask of claim 4, wherein the sidewalls of the mask body further comprise a plurality of recessed areas, and the plurality of rib members are configured to have conforming shapes to tightly press-fit within the plurality of recessed areas.

6. The ventilation mask of claim 1, wherein the interface member is ring-shaped, and the elbow comprises an outer wall having at least one snap protrusion near the second end, the at least one snap protrusion configured to interlock with the interface member.

7. The ventilation mask of claim 6, wherein the at least one snap protrusion comprises a plurality of snap protrusions equally spaced apart from each other along a periphery of the outer wall of the elbow.

8. The ventilation mask of claim 1, further comprising:
a pad member configured to engage a forehead of the patient to stabilize a position of the ventilation mask on the patient; and
an arm member connecting the pad member to the frame.

9. The ventilation mask of claim 8, further comprising a hinge connecting the pad member to the arm member so that the mask body and the frame can be moved away from the face of the patient to expose at least the mouth and the nose while the pad member remains secured to the forehead.

10. The ventilation mask of claim 1, wherein the elbow comprises a valve configured to release and open the elbow to atmosphere when the gas supply is disrupted.

11. The ventilation mask of claim 1, wherein the mask body and the frame are comprised of silicone.

12. A method of assembling a ventilation mask comprising a mask body having a first opening, a frame having an interface member, and an elbow having a first end and a second end, the mask body comprises a grooved portion disposed around the first opening, the interface member comprises a protruding flange, and the second end of the elbow has a flange, the method comprising:
connecting the frame to an outer surface of the mask body and so that the interface member is interlocked with the mask body at the first opening, the connecting comprising press-fitting the protruding flange within the grooved portion to interlock and seal the interface member with the mask body;
pulling the first end of the elbow from inside the mask body through the first opening and the interface member; and
fixedly securing the second end of the elbow to the interface member, wherein fixedly securing comprises holding the grooved portion against the protruding flange of the interface member with the flange.

13. The method of claim 12, wherein the frame comprises a base member, and a plurality of undercuts are disposed along sidewalls of the mask body, wherein connecting further comprising interlocking the base member with the plurality of undercuts.

14. The method of claim 12, wherein the elbow comprises a plurality of snap protrusions equally spaced apart from each other along a periphery of the outer wall near the second end, wherein fixedly securing further comprising interlocking the plurality of snap protrusions with the interface member.

* * * * *